United States Patent [19]

Waller

[11] Patent Number: 5,227,517
[45] Date of Patent: Jul. 13, 1993

[54] PROCESS FOR PREPARING ETHYLIDENE DIACETATE USING IODIDE CATALYSTS

[75] Inventor: Francis J. Waller, Allentown, Pa.

[73] Assignee: Air Products and Chemicals, Inc., Allentown, Pa.

[21] Appl. No.: 870,006

[22] Filed: Apr. 15, 1992

[51] Int. Cl.⁵ .............................................. C07C 67/00
[52] U.S. Cl. ................................................. 560/238
[58] Field of Search ....................................... 560/238

[56] References Cited

U.S. PATENT DOCUMENTS

| | | | |
|---|---|---|---|
| 2,021,698 | 11/1935 | Perkins | 560/238 |
| 2,859,241 | 11/1958 | Schnizer | 260/491 |
| 2,860,159 | 11/1958 | Sharp | 560/238 |
| 4,843,170 | 6/1989 | Isshiki et al. | 560/261 |

FOREIGN PATENT DOCUMENTS 0028515  3/1984  European Pat. Off.

OTHER PUBLICATIONS

Hydrocarbon Process (1965) vol. 44, p. 287.
Chem. Abstracts 1967-91, vol. 114, #4, Ukr. Khim. Zh., vol. 56(1) pp. 101-103.

Primary Examiner—Michael L. Shippen
Attorney, Agent, or Firm—Keith D. Gourley; James C. Simmons; William F. Marsh

[57] ABSTRACT

The present invention relates to a process for producing ethylidene diacetate (EDDA) wherein at least one process step comprises condensing a feedstock of acetaldehyde and acetic anhydride in the presence of acetic acid and an iodide catalyst selected from the group consisting of potassium iodide, lithium iodide, methyl iodide and mixtures thereof. In a preferred embodiment, EDDA is prepared in an integrated process wherein the previously mentioned feedback is prepared by reacting dimethyl ether and acetic acid to form a first intermediate product mixture and hydrocarbonylating the first intermediate product mixture to form the condensation feedstock.

13 Claims, No Drawings

PROCESS FOR PREPARING ETHYLIDENE DIACETATE USING IODIDE CATALYSTS

FIELD OF THE INVENTION

This invention relates to a process for producing ethylidene diacetate by condensing acetaldehyde and acetic anhydride in the presence of an iodide catalyst utilizing acetic acid as a solvent.

BACKGROUND OF THE INVENTION

Ethylidene diacetate (EDDA) is a valuable chemical which can be used as an intermediate in preparing a wide variety of commercially valuable compositions such as vinyl acetate and acetic acid. Considerable interest has been focused on developing improved processes for preparing EDDA wherein problems associated with prior art methods can be overcome.

The condensation reaction of acetaldehyde and acetic anhydride to EDDA is a known chemical reaction catalyzed, for example, by Lewis and protonic acids. U.S. Pat. No. 2,859,241 discloses a process for preparing EDDA wherein acetaldehyde and an alkanoic anhydride such as acetic anhydride are reacted in the presence of an aromatic sulfonic acid such as benzenesulfonic acid to produce EDDA. A commercial process based on the foregoing disclosure is described in Hydrocarbon Process 44 (1965) 287.

U.S. Pat. No. 4,843,170 discloses a process for preparing EDDA wherein acetaldehyde and/or dimethylacetal and acetic anhydride are reacted to form EDDA as a reaction intermediate wherein EDDA is further cracked to form vinyl acetate. While no catalysts are required in the EDDA step, the reference states that acid catalysts such as a Bronsted acids, i.e. HI, HBr, HCl, HF, $H_2SO_4$, $HNO_3$, $H_3PO_4$, $H_3BO_3$, $HClO_3$, $HBrO_3$, $HIO_3$, polyphosphoric acid, benzenesulfonic acid and alkylbenzenesulfonic acid or Lewis acids of halides having a central atom selected from Groups IIa, IIIa, IVa, Va, IIIb, IVb, Vb, VIb, VIIb and VIII of the Periodic Table can be used.

European Patent Specification No. 0 028 515 teaches a process for producing EDDA wherein one or a mixture of compounds selected from (1) dimethyl acetal, (2) acetaldehyde and methyl acetate, and (3) acetaldehyde and dimethyl ether are reacted in the presence of a catalyst. Suitable catalysts comprise compounds formed from at least one metal belonging to Group VIII of the Periodic Table and at least one compound selected from iodides, bromides and mixtures thereof.

Chem. Abstracts 1967-91, Vol. 114, #4, of a Russian article, Ukr. Khim.Zh., Vol. 56(1), pages 101-3 discloses that the reaction rate of acetaldehyde with acetic anhydride is inhibited in the presence of alkali-metal or alkali earth metal salts. The inhibiting activity decreases in the series of $K \sim Na \sim L > Ba > Sr > Ca > Mg > Al$ and such inhibiting effect was stated to be independent of the anion. Data presented in these Russian studies would lead to the conclusion that alkali metal iodides inhibit the reaction between acetaldehyde and acetic anhydride.

The prior art describes the carbonylation and hydrocarbonylation of methyl acetate to acetic anhydride and methyl acetate to form EDDA, respectively. In addition, mixtures of methyl acetate (MA) and dimethyl ether (DME) or dimethyl ether by itself are often mentioned as equivalent feedstocks. However, dimethyl ether and methyl acetate are not chemically equivalent feedstocks. Group VIII catalysts, organic iodides, synthesis gas composition, reaction temperatures and pressures, and dipolar solvents play a potential role differentiating the reactivity of DME and MA.

Considerable interest abounds in discovering a process for preparing EDDA in high yield under substantially anhydrous conditions. The instant patent application presents a process which overcomes many of the limitations associated with prior art processes. Specifically, the instant process provides high selectivity to EDDA and can be practiced utilizingg a broad range of feedstocks.

SUMMARY OF THE INVENTION

The present invention relates to a process for producing ethylidene diacetate (EDDA) wherein at least one process step comprises condensing a feedstock of acetaldehyde and acetic anhydride in the presence of acetic acid and an iodide catalyst selected from the group consisting of potassium iodide, lithium iodide, methyl iodide and mixtures thereof. The condensation reaction can be performed over a wide range of temperatures depending upon the particular activity of the iodide catalyst used and its solubility in acetic acid. Suitable reaction conditions for practicing the condensation step include any combination of temperatures and pressures capable of producing the desired product, EDDA. Suitable process temperatures range from about 20° C. to about 275° C. and suitable pressures range from atmospheric to about 3000 psig. Depending upon the operating temperature and pressure, the process can be carried out in the liquid or vapor phase.

Applicant has further discovered various alternate embodiments wherein the components of the condensation feedstock are obtained by one or more initial reaction steps. In a first alternate embodiments, the condensation feedstock is produced by hydrocarbonylating methyl acetate and dimethyl ether under specified reaction conditions. The process of this embodiment comprises (a) reacting a feedstock comprising methyl acetate, dimethyl ether, hydrogen and carbon monoxide in the presence of a hydrocarbonylation catalyst under conditions sufficient to form a first intermediate product mixture comprising acetic acid, acetic anhydride and acetaldehyde; (b) condensing the first intermediate product mixture in the presence of an iodide catalyst selected from the group consisting of potassium iodide, lithium iodide and methyl iodide under reaction conditions sufficient to form a second intermediate product mixture comprising ethylidene diacetate; and (c) recovering the ethylidene diacetate from the second intermediate product mixture.

In another alternate embodiment, the condensation feedstock is produced by effecting an alkylation reaction between dimethyl ether and acetic acid to form a product mixture comprising methyl acetate, dimethyl ether and methanol followed by a hydrocarbonylation of the product mixture to form the feedstock. The process of this embodiment comprises: (a) reacting dimethyl ether and acetic acid in the presence of an alkylation catalyst under reaction conditions sufficient to form a first intermediate product mixture comprising methyl acetate, dimethyl ether and methanol; (b) reacting the first intermediate product mixture with hydrogen and carbon monoxide in the presence of a hydrocarbonylation catalyst under conditions sufficient to form a second intermediate product mixture comprising acetic acid, acetic anhydride and acetaldehyde; (c) condensing the second intermediate product mixture in the presence of an iodide catalyst selected from the group consisting of potassium iodide, lithium iodide, methyl iodide under reaction conditions sufficient to form a third intermediate product mixture comprising ethylidene diacetate; and (d) recovering the ethylidene diacetate from the third intermediate product mixture.

DETAILED DESCRIPTION OF THE INVENTION

The present invention relates to a process for producing ethylidene diacetate (EDDA) wherein at least one process step comprises condensing a feedstock of acetaldehyde and acetic anhydride in the presence of acetic acid as a solvent and an iodide catalyst selected from the group consisting of potassium iodide, lithium iodide, methyl iodide and mixtures thereof. The condensation reaction can be performed over a wide range of temperatures and pressures depending upon the particular activity of the iodide catalyst used and its solubility in acetic acid.

The reaction can be carried out in the vapor phase or the liquid phase using any combination of temperatures and pressures at which the reaction proceeds to form EDDA. The reaction typically is conducted from 20° C. to about 275° C. and a pressure ranging from atmospheric to about 3000 psig. Preferably, the condensation is effected at a temperature ranging from 130° C. to about 230° C. and a pressure ranging from atmospheric to about 2100 psig. The ratio of acetaldehyde to acetic anhydride is not critical to practicing the present invention. Typical molar ratios of acetaldehyde to acetic anhydride range from 1:40 to about 40:1. The condensation step can be carried out in a wide variety of reactors in a batch or continuous mode using an autoclave type reactor and fixed bed reactors wherein the product can be removed continuously by distillation during the reaction.

Applicant has discovered that the condensation between acetaldehyde and acetic anhydride proceeds advantageously in the presence of acetic acid and that acetic acid also serves as a reaction solvent providing unexpectedly superior selectivity over the same reaction conducted in the absence of acetic acid. However, as evidenced by the data presented herein, the condensation step will occur in the absence of acetic acid. Those of ordinary skill in the art will appreciate that the condensation step can be effected in the presence of any inert solvent. The term, inert solvents, refers to a medium which will not react with the specified reactants and EDDA under the specified reaction conditions.

While the reactants of the present invention are readily available commercially, Applicant has further discovered two alternate process embodiments which disclose integrated processes for producing EDDA. In the first alternate embodiment, the condensation feedstock is produced by hydrocarbonylating methyl acetate and dimethyl ether. In a second alternate embodiment, methyl acetate and dimethyl ether, used as a feedstock during the hydrocarbonylation, is prepared by reacting dimethyl ether and acetic acid in the presence of an alkylation catalyst.

According to the first alternate embodiment, a process is disclosed for preparing EDDA which comprises (a) reacting a feedstock comprising methyl acetate, dimethyl ether, hydrogen and carbon monoxide in the presence of a hydrocarbonylation catalyst under conditions sufficient to form a first intermediate product mixture comprising acetic acid, acetic anhydride and acetaldehyde; (b) condensing the first intermediate product mixture in the presence of an iodide catalyst selected from the group consisting of potassium iodide, lithium iodide and methyl iodide under reaction conditions sufficient to form a second intermediate product mixture comprising ethylidene diacetate; and (c) recovering the ethylidene diacetate from the second intermediate product mixture.

The hydrocarbonylation reaction presented in step (a) of the first alternate embodiment can be operated under a broad range of reaction conditions using any of the hydrocarbonylation catalysts disclosed in the art. Representative references which teach suitable conditions and catalytic systems for practicing the hydrocarbonylation step include U.S. Pat. Nos. 4,429,150 and 4,323,697 and British Patent Specification No. 1,538,782. Typical reaction conditions comprise a temperature ranging from about 20° C. to about 220° C. and a pressure ranging from about 100 psig to about 3000 psig.

A preferred catalyst for conducting the hydrocarbonylation of methyl acetate and dimethyl ether is a catalyst system consisting essentially of a Group VIII metal, methyl iodide, lithium iodide and optionally, lithium acetate. A particularly preferred source of the Group VIII metal is rhodium (III) chloride trihydrate. More details regarding the preferred catalyst system for practicing the hydrocarbonylation step are presented in copending U.S. patent application 07/870,126, entitled, "Process for Converting Dimethyl Ether to Ethylidene Diacetate", assigned to Air Products and Chemicals, Inc., Allentown, Pa., filed on Apr. 15, 1992, the specification which is incorporated by reference herein.

The second alternate embodiment incorporates an additional step to the first alternate embodiment wherein the methyl acetate and dimethyl ether used as a feedstock in the hydrocarbonylation step is prepared by alkylating dimethyl ether and acetic acid in the presence of an alkylation catalyst. This embodiment comprises (a) reacting dimethyl ether and acetic acid in the presence of an alkylation catalyst under reaction conditions sufficient to form a first intermediate product mixture comprising methyl acetate, dimethyl ether and methanol; (b) reacting the first intermediate product mixture with hydrogen and carbon monoxide in the presence of a hydrocarbonylation catalyst under conditions sufficient to form a second intermediate product mixture comprising acetic acid, acetic anhydride and acetaldehyde; (c) condensing the second intermediate product mixture in the presence of an iodide catalyst selected from the group consisting of potassium iodide, lithium iodide, methyl iodide under reaction conditions sufficient to form a third intermediate product mixture comprising ethylidene diacetate; and (d) recovering the ethylidene diacetate from the third intermediate product mixture. Optionally, the methanol may be separated from the first intermediate product mixture according to step (a) prior to effecting step (b).

The alkylation step according to the second alternate embodiment can be operated under a broad range of reaction conditions using any of the alkylation catalysts disclosed in the art. Representative references which teach suitable conditions and catalytic systems for practicing the alkylation step include U.S. Pat. No. 3,510,511. The preferred alkylation catalyst consists essentially of an iodide of a Group IA element wherein the reacting is conducted at a temperature ranging of 100° to about 400° C. and a pressure ranging from 1 atmosphere to about 150 atmospheres. More details regarding t he preferred catalyst system for practicing the alkylation step are presented in copending U.S. patent application Ser. No. 07/868,914, entitled, "Process for Producing Organic Esters By Reacting a Carboxylic Acid and a Dialkyl Ether", assigned to Air Products and Chemicals, Inc., Allentown, Pa., filed on Apr. 15, 1992, the specification which is incorporated by reference herein.

The following examples are given to illustrate the process of the present invention and should not be construed as limiting the scope.

EXAMPLES

Experimental Procedure

The reaction products and acetic acid were analyzed by DB-1701 FSOT capillary column interfaced to a flame ionization detector. Quantitation was obtained using an internal standard technique. The lower limit of detection for the components of interest was approximately 0.002 wt. %. All organic compound structures were verified by gas chromatography/mass spectrometry (GC/MS).

A 300 cc Hastelloy C autoclave was equipped with a dip tube, thermocouple, cooling coils, a belt driven magnetic stirrer and an inlet for gases. The autoclave was protected from overpressure by a rupture disk and a relief valve. All inlet lines, valves and other surfaces being exposed to methyl iodide were made of either Hastelloy C or Inconel.

The following general procedure was used to load, pressurize, run and unload the autoclave. The autoclave was charged with acetic acid or toluene, Group 1A salts, methyl iodide, HI in acetic acid or other components mentioned in the Tables below. The autoclave was sealed, pressurized with nitrogen to test for leaks, vented, pressurized with a synthesis gas (syn-gas) premix or CO or $N_2$ at least thrice, and vented to approximately 20 psi. In conducting the condensation step, acetaldehyde and acetic anhydride were transferred to the autoclave. While stirring, the reactor pressure was increased to 300–400 psi and the temperature was brought up to operating temperature. At operating temperature, the pressure was increased to operating pressure and the condensation reaction was run for the desired length of time. The autoclave was maintained at constant pressure. Following completion of the reaction, the autoclave was cooled to room temperature, depressurized and the contents were poured from the reactor. The reactor was rinsed with 25 ml acetic acid or toluene and combined with the reactor discharge.

EXAMPLES 1-9

Examples 1 through 9, summarized in Table 1, illustrate the condensation steps of the various process embodiments the claimed invention. Example 1 shows that the subject condensation reaction occurred with 55.8% selectivity in the absence of a catalyst in a solvent of acetic acid. Example 2 shows that practically no condensation reaction occurred between acetaldehyde (AcH) and acetic anhydride ($Ac_2O$) without a catalyst when toluene was used as a solvent. Example 3 demonstrates that selectivity to EDDA was reduced to 0.6% when HI was used as a catalyst in acetic acid. Both LiI (Example 8) and KI (Example 9) catalysts in acetic acid each gave 100% EDDA selectivity, but selectivity fell to 21.6% using LiOAc (Example 4). Selectivity to EDDA was 61.5% when $CH_3I$ was used as a catalyst (Example 7), but selectivity fell to 33.1 and 39.5% with NaI and CsI, respectively.

This data demonstrate that the efficiency of the iodide catalysts for the subject condensation reaction increases according to the series LiI>KI>$CH_3I$>LiOAc>CsI>NaI>>HI. This observed trend is contrary to that reported in Chem. Abstracts 1967-91, Vol. 114, #4, of Russian article, Ukr, Khim.Zh., Vol. 56(1), pp. 101-3 which discloses that the reaction rate of acetaldehyde with acetic anhydride is inhibited in the presence of alkali-metal or alkali earth metal salts. The inhibiting activity according to the prior reference was found to decrease in the series of K~Na~Li>Ba>Sr>Ca>Mg>Al and such inhibiting effect was stated to be independent of the anion. Applicant has unexpectedly discovered that the catalytic activity of the subject Group IA iodides is reversed when acetic acid is used as a solvent during the condensation reaction. Applicants' claimed invention thus pertains to a process for preparing EDDA utilizing a condensation reaction between acetic anhydride and acetaldehyde wherein a novel group of catalysts are used and wherein acetic acid is necessarily used as a reaction medium.

TABLE 1

Iodide Catalysts for EDDA Formation

| Ex. No. | Charged, mmol | | Catalyst* (mmol) | $Ac_2O$ Conv. | EDDA Sel. |
|---|---|---|---|---|---|
| | AcH | $Ac_2O$ | | | |
| 1 | 39.8 | 37.7 | None | 54.1 | 55.8 |
| 2 | 36.4 | 35.8 | None [Toluene] | 2.8 | 9.0 |
| 3 | 35.0 | 35.5 | HI (11.6) | 99.7 | 0.6 |
| 4 | 34.5 | 34.3 | LiOAc (11.4) | 55.4 | 21.6 |
| 5 | 35.2 | 34.8 | CsI (7.3) | 63.2 | 39.5 |
| 6 | 35.2 | 35.3 | NaI (7.5) | 71.9 | 33.1 |
| 7 | 33.4 | 34.6 | MeI (11.8) | 84.1 | 61.5 |
| 8 | 35.7 | 35.0 | LiI (14.9) | 100 | 100 |
| 9 | 35.2 | 36.5 | KI (11.7) | 55.0 | 100 |

*Reaction temp: 175° C.; reaction time: 75 min.; reaction pressure: 1500 psi $N_2$
Solvent: 135 ml HOAc unless noted differently in [ ]

EXAMPLES 10-15

Examples 10-15, set forth in Table 2, demonstrate the hydrocarbonylation reaction for producing the disclosed condensation feedstock. More particularly, DME is hydrocarbonylated using a $CO/H_2$ mix of 1:1 in the presence of the enumerated catalyst systems in acetic acid. In the selectivity calculation, Σ(mmol products) was calculated according to the sum of (MeOAc+$Ac_2O$+AcH+EDDA) and is based upon the DME required to form each product. According to Examples 10, 11 and 15 of Table 2 and Example 16 of Table 3, an upside down volcano relationship was found to exist between EDDA selectivity and mol % LiI/(mol LiI+mol MeI) used in the catalyst system wherein the ratio of DME to MeI was held constant.

TABLE 2

| Ex. No. | Charged | | Catalyst System | | Rxn.* Time (hr.) |
|---|---|---|---|---|---|
| | DME (mmol) | LiI (mmol) | Group VIII (mmol) | MeI (mmol) | |
| 10 | 102 | 19.6 | $RhCl_3.3H_2O$ 0.76 | 65.5 | 0.75 |
| 11 | 124 | 3.7 | $RhCl_3.3H_2O$ 0.76 | 63.8 | 0.75 |
| 12 | 193 | 14.9 | $RhCl_3.3H_2O$ 0.76 | 63.4 | 0.75 |
| 13 | 176 | 11.2 | $RhCl_3.3H_2O$ 0.76 | 78.2 | 0.75 |

TABLE 2-continued

| Ex. No. | | | Catalyst System | | |
|---|---|---|---|---|---|
| 14 | 204 | 11.2 | RhCl$_3$.3H$_2$O 0.76 | 78.9 | 1.5 |
| 15 | 122 | 14.9 | RhCl$_3$.3H$_2$O 0.76 | 63.4 | 0.75 |

| Ex. No. | % Yield on Charged DME | % Selectivity | | | |
|---|---|---|---|---|---|
| | | MA | Ac$_2$O | AcH | EDDA |
| 10 | 75.9 | 15.2 | 25.9 | 0.1 | 58.8 |
| 11 | 74.5 | 33.5 | 11.6 | 0.1 | 54.8 |
| 12 | 86.7 | 63.7 | 20.4 | 0.1 | 15.8 |
| 13 | 78.9 | 46.7 | 12.5 | 0.1 | 40.8 |
| 14 | 66.1 | 20.6 | 1.0 | 5.2 | 73.2 |
| 15 | 78.9 | 31.9 | 27.8 | 0.1 | 40.2 |

*Stirring rate: 1600 rpm; rxn. temp.: 175° C.; rxn. press.: 1500 psi; Acetic acid: 2.40–2.43 mols.

EXAMPLES 16-19

Examples 16-19, set forth in Table 3, further disclose runs of the hydrocarbonylation step of the integrated process for producing EDDA wherein a CO/H$_2$ mix of 1:1 was used. The Examples demonstrate results obtained by reacting DME, acetic acid, hydrogen and carbon monoxide in the presence of the enumerated catalyst systems. The number of mmol of EDDA as defined in Table 3 was the actual amount of DME required to prepare the GC measured amount of EDDA. The reported amount of acetic acid in Table 3 is the incremental amount above the charged acetic acid and corresponds to the amount expected when EDDA and acetic acid are coproduced.

TABLE 3

| Ex. No. | Charged DME (mmol) | Catalyst System | | MeI (mmol) | Rxn. Time (hr) |
|---|---|---|---|---|---|
| | | LiI (mmol) | Group VIII (mmol) | | |
| 16 | 139 | 10.7 | RhCl$_3$.3H$_2$O 0.76 | 63.5 | 0.75 |
| 17 | 111 | 14.9 | RhCl$_3$.3H$_2$O 0.76 | 65.1 | 0.75 |
| 18 | 246 | 11.2 | RhCl$_3$.3H$_2$O 0.76 | 77.5 | 1.5 |
| 19 | 291 | 14.9 | RhCl$_3$.3H$_2$O 0.76 | 63.4 | 4.0 |

| Ex. No. | MA | Ac$_2$O | AcH | EDDA | HOAc |
|---|---|---|---|---|---|
| | | | mmol | | |
| 16 | 41.5 | 28.1 | 0.1 | 36.9 | 18.3 |
| 17 | 16.0 | 13.1 | 0.2 | 48.9 | 24.3 |
| 18 | 73.5 | 1.0 | 13.9 | 88.8 | 40.0 |
| 19 | 61.9 | 1.9 | 21.9 | 120.2 | 81.6 |

| Ex. No. | % Yield on Charged DME | % Selectivity | | | |
|---|---|---|---|---|---|
| | | MA | Ac$_2$O | AcH | EDDA |
| 16 | 76.7 | 38.9 | 26.4 | 0.1 | 34.6 |
| 17 | 70.5 | 20.5 | 16.8 | 0.3 | 62.5 |
| 18 | 72.0 | 41.5 | 0.7 | 7.8 | 50.1 |
| 19 | 70.7 | 30.0 | 0.9 | 10.6 | 58.3 |

Rxn. temp.: 160° C.; Acetic acid: 2.40–2.43 mols.

EXAMPLES 20-23

Examples 20-23, set forth in Table 4, illustrate the effect of a hydrogen-rich atmosphere (75 mol %) on organic product distribution obtained by the hydrocarbonylation step of the present invention. In particular, use of more than 75 mol % H$_2$ causes greater amounts of EtOAc to be produced along with EtI. The data demonstrate that the present process is preferably run using a 1:1 to about 4:1 molar ratio of carbon monoxide to hydrogen, meaning that the hydrocarbonylation should be run rich in carbon monoxide over hydrogen.

TABLE 4

| Ex. No. | Charged DME (mmol) | Catalyst System | | MeI (mmol) | Rxn. Time (hr) |
|---|---|---|---|---|---|
| | | LiI (mmol) | Group VIII (mmol) | | |
| 20 | 126 | 11.2 | RhCl$_3$.3H$_2$O 0.76 | 77.5 | 1.5 |
| 21 | 117 | 11.2 | RhCl$_3$.3H$_2$O 0.76 | 78.5 | 1.5 |
| 22 | 122 | 11.2 | RhCl$_3$.3H$_2$O 0.76 | 63.9 | 1.5 |
| 23 | 126 | 14.9 | RhCl$_3$.3H$_2$O 0.76 | 64.2 | 0.75 |

| Ex. No. | CO:H$_2$ | MA | Ac$_2$O | AcH | EDDA | EtOAc | EtI |
|---|---|---|---|---|---|---|---|
| | | | | mmol | | | |
| 20 | 1:1 | 0.6 | 0.3 | 13.7 | 7.7 | 4.2 | 9.3 |
| 21 | 1:3 | 0.1 | — | 0.3 | — | 0.9 | 26.7 |
| 22 | 1:3 | — | — | — | — | 1.5 | 26.6 |
| 23 | 1:3 | 6.8 | — | 4.3 | — | 6.3 | 6.1 |

EXAMPLES 24-32

Runs 24 through 32 in Table 5 illustrate the alkylation step of the integrated process for producing EDDA wherein acetic acid and dimethyl ether are reacted in the absence of a catalyst, in the presence of a catalyst consisting essentially of an iodide of a Group IA element and in the presence of lithium acetate. The reactions were run at a temperature of 175° C. under the enumerated atmospheres. Runs 24 and 25, conducted in the absence of a catalyst, demonstrate that essentially no methyl acetate (MA) is formed under the enumerated reaction conditions and that the presence of a CO atmosphere provides only a minor effect upon the formation of methyl acetate. Runs 26 through 29 demonstrate that dimethyl ether is converted to methyl acetate in the presence of LiI under atmosphere of either CO, N$_2$ or CO/H$_2$. Runs 29 and 30 demonstrate that similar product distributions were obtained with either HI or LiI when the atmosphere was 50% CO in H$_2$. Under the reaction conditions according to Runs 24 through 32, dimethyl ether did not directly react with CO to give methyl acetate and LiOAc was essentially ineffective in producing methyl acetate, especially when compared with LiI.

TABLE 5

REACTION OF ACETIC ACID AND DIMETHYL ETHER WITH GROUP IA IODIDE CATALYSTS

| Run | Charged* DME (mmol) | Atmosphere (psig) | Catalyst (mmol) | Product Distribution | | | Rxn. Time (min.) |
|---|---|---|---|---|---|---|---|
| | | | | MA | Ac$_2$O | MeI | |
| | | | | mmol | | | |
| 24 | 130 | N$_2$, 1500 | None | — | — | — | 75 |
| 25 | 120 | CO, 1500 | None | 1.6 | — | 0.1 | 75 |
| 26 | 102 | N$_2$, 1500 | LiI (14.9) | 16.5 | — | 8.2 | 75 |
| 27 | 122 | CO, 1500 | LiI (7.5) | 12.9 | 0.1 | 7.1 | 45 |
| 28 | 226 | N$_2$, 1500 | LiI (14.9) | 25.6 | — | 11.6 | 75 |
| 29 | 122 | CO/H$_2$, 1500 | LiI (14.9) | 20.4 | — | 10.4 | 45 |
| 30 | 109 | CO/H$_2$, 1500 | HI (16.0) | 15.4 | — | 13.4 | 45 |
| 31 | 122 | N$_2$, 1500 | LiOAc (11.4) | 0.6 | — | — | 75 |
| 32 | 128 | CO/H$_2$, | LiOAc | 0.4 | — | 0.1 | 45 |

TABLE 5-continued
REACTION OF ACETIC ACID AND DIMETHYL ETHER WITH GROUP IA IODIDE CATALYSTS

| Run | Charged* DME (mmol) | Atmosphere (psig) | Catalyst (mmol) | Product Distribution | | | Rxn. Time (min.) |
|---|---|---|---|---|---|---|---|
| | | | | MA | Ac₂O mmol | MeI | |
| | | 1500 | (22.7) | | | | |

*2.35–2.45 mol acetic acid
MA: Methyl acetate
Ac₂O: Acetic anhydride
MeI: Methyl iodide While the embodiments of process of the present process have been disclosed with reference to specific examples, one of ordinary skill can make various changes and modifications to the invention to adapt it to various uses and conditions. As such, these changes and modifications are properly, equitably, and intended to be, within the full range of equivalents of the following claims.

I claim:

1. A process for producing ethylidene diacetate which comprises:
   (a) condensing a feedstock comprising acetaldehyde and acetic anhydride in the presence of acetic acid and an iodide catalyst selected from the group consisting of potassium iodide, lithium iodide, methyl iodide and mixtures thereof under reaction conditions sufficient to form a reaction mixture comprising ethylidene diacetate; and
   (b) recovering the ethylidene diacetate from the reaction mixture.

2. The process according to claim 1 wherein the reaction conditions comprise a temperature ranging from about 20° C. to about 275° C. and a pressure ranging from atmospheric to about 3000 psig.

3. The process according to claim 2 wherein the acetaldehyde and acetic anhydride are reacted in a molar ratio ranging from 1:40 to about 40:1.

4. The process according to claim 3 wherein the reaction conditions comprise a temperature ranging from about 130° to 230° C. and a pressure ranging from atmospheric to about 2,100 psi.

5. A process for producing ethylidene diacetate which comprises:
   (a) reacting a feedstock comprising methyl acetate, dimethyl ether, hydrogen and carbon monoxide in the presence of a hydrocarbonylation catalyst under conditions sufficient to form a first intermediate product mixture comprising acetic acid, acetic anhydride and acetaldehyde;
   (b) condensing the first intermediate product mixture in the presence of an iodide catalyst selected from the group consisting of potassium iodide, lithium iodide and methyl iodide under reaction conditions sufficient to form a second intermediate product mixture comprising ethylidene diacetate; and
   (c) recovering the ethylidene diacetate from the second intermediate product mixture.

6. The process according to claim 5 wherein reaction conditions according to step (a) comprise a temperature ranging from about 20° C. to about 220° C. and a pressure ranging from about 100 psig to about 3000 psig.

7. The process according to claim 6 wherein the hydrocarbonylcation catalyst consists essentially of a Group VIII metal, methyl iodide and lithium iodide.

8. The process according to claim 7 wherein the source of the Group VIII metal is rhodium(III) chloride trihydrate.

9. The process according to claim 8 wherein the hydrocarbonylation catalyst further comprises lithium acetate.

10. A process for producing ethylidene diacetate which comprises:
    (a) reacting dimethyl ether and acetic acid in the presence of an alkylation catalyst under reaction conditions sufficient to form a first intermediate product mixture comprising methyl acetate, dimethyl ether and methanol;
    (b) reacting the first intermediate product mixture with hydrogen and carbon monoxide in the presence of a hydrocarbonylation catalyst under conditions sufficient to form a second intermediate product mixture comprising acetic acid, acetic anhydride and acetaldehyde;
    (c) condensing the second intermediate product mixture in the presence of an iodide catalyst selected from the group consisting of potassium iodide, lithium iodide, methyl iodide under reaction conditions sufficient to form a third intermediate product mixture comprising ethylidene diacetate; and
    (d) recovering the ethylidene diacetate from the third intermediate product mixture.

11. The process according to claim 10 further comprising:
    (e) separating methanol from the first intermediate product mixture according to step (a) prior to effecting step (b).

12. The process according to claim 10 wherein the alkylation catalyst consists essentially of an iodide of a Group IA element and wherein the reacting is conducted at a temperature ranging of 100° to about 400° C. and a pressure ranging from 1 atmosphere to about 150 atmospheres.

13. The process according to claim 12 wherein the alkylation catalyst consists essentially of a solid phase acid catalyst having an acidity factor of at least 0.30 and wherein the reacting is conducted at a temperature ranging from 100° to about 400° C. and a pressure ranging from 1 atmospheres to about 150 atmospheres.

* * * * *